(12) United States Patent
Hoshino

(10) Patent No.: US 7,541,500 B2
(45) Date of Patent: Jun. 2, 2009

(54) METHOD FOR PRODUCING CYCLOALKANOL AND/OR CYCLOALKANONE

(75) Inventor: Masahiro Hoshino, Ehime-ken (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/710,413

(22) Filed: Feb. 26, 2007

(65) Prior Publication Data

US 2007/0225526 A1 Sep. 27, 2007

(30) Foreign Application Priority Data

Feb. 27, 2006 (JP) ............... 2006-049952

(51) Int. Cl.
*C07C 45/27* (2006.01)
*C07C 35/08* (2006.01)

(52) U.S. Cl. ..................... 568/360; 568/836

(58) Field of Classification Search .......... 568/360, 568/836

See application file for complete search history.

(56) References Cited

U.S. PATENT DOCUMENTS 6,160,183 A * 12/2000 Druliner et al. ............. 568/360

FOREIGN PATENT DOCUMENTS

| EP | 1 707 553 A | 10/2006 |
|---|---|---|
| GB | 2 427 192 A | 12/2006 |
| JP | 2003-261484 A | 9/2003 |
| WO | WO 92/16487 A1 | 10/1992 |
| WO | WO 98/04538 A1 | 2/1998 |
| WO | WO 99/40055 A1 | 8/1999 |
| WO | WO 02/16296 A1 | 2/2002 |
| WO | WO 02/16298 A1 | 2/2002 |

OTHER PUBLICATIONS

R. Raja, et al., "Powerful Redox Molecular Sieve Catalysts for the Selective Oxadation of Cyclohexane in Air", J. Am. Chem. Soc., vol. 121, (1999), pp. 11926-11927.
R. Zhao, et al., "A highly efficient oxidation of cyclohexane over Au/ZSM-5 molecular sieve catalyst with oxygen as oxidant", Chem. Comm., (2004), pp. 904-905.
G. Qian et al., "Oxidation of Cyclohezane over Bi-incorporated MCM-41 Mesoporous Molecular Sieve Catalyst with Oxygen as Oxidant", Chemistry Letters vol. 34, No. 2, (2005), pp. 162-163.
G. Lu[a], et al.., "Gold nanoparticles in mesoporous materials showing catalytic selective oxidation cyclohexane using oxygen", Applied Catalysis A: General 280, (2005), pp. 175-180.
L. Zhou, et al., "Catalytic oxidation of cyclohexane to cyclohexanol and cyclohexanone over $Co_3O_4$ nanocrystals with molecular oxygen", Applied Catalysis A: General 292, (2005), pp. 223-228.
Y. Kurusu et al., "Functionalization of Silica Gel: Application for the Catalytic Oxidation of Alkanes[1]", Journal of Organic Chemistry, American Chemical Society, vol. 56, No. 6, (Mar. 15, 1991), pp. 1981-1983.

* cited by examiner

*Primary Examiner*—Sikarl A Witherspoon
(74) *Attorney, Agent, or Firm*—Sughrue Mion, PLLC

(57) ABSTRACT

In case of oxidizing cycloalkane with oxygen, the catalyst to be used is a catalyst obtained by supporting metals of Groups 5 to 10 of the Periodic Table on a carrier, the carrier being subjected to a catalytic treatment with an organosilicon compound. The metal is preferably vanadium, chromium, manganese, iron, cobalt, ruthenium or palladium, while the carrier is preferably an oxide of magnesium, aluminum, silicon, titanium or zirconium.

8 Claims, 1 Drawing Sheet

METHOD FOR PRODUCING CYCLOALKANOL AND/OR CYCLOALKANONE

BACKGROUND OF THE INVENTION

1. Field of the Invention

The present invention relates to a method for producing cycloalkanol and/or cycloalkanone by oxidizing cycloalkane with oxygen.

2. Description of the Related Art

As a method for producing cycloalkanol and/or cycloalkanone by oxidizing cycloalkane with oxygen, for example, there has been known a method of performing the oxidation in a homogeneous system using, as a catalyst, a soluble metal compound such as cobalt carbonate for a long time. Various studies have been made on the oxidation in a heterogeneous system using a solid catalyst and, as the solid catalyst, various catalysts such as metal oxide catalysts and metal supported catalysts have been proposed (see, for example, EP0916 403A; WO99/040055; Japanese Unexamined Patent Publication (Kokai) No. 2003-261484; *Journal of American Chemical Society*, (U.S.A.), 1999, Vol. 121, pp. 11926-11927; *Chemical Communications* (U.K.), 2004, pp. 904-905; *Chemistry Letters*, 2005, Vol. 34, pp. 162-163; *Applied Catalysis A: General* (Netherlands), 2005, Vol. 280, pp. 175-180; and *Applied Catalysis A: General* (Netherlands), 2005, Vol. 292, pp. 223-228).

DISCLOSURE OF THE INVENTION

The above-mentioned conventional methods include unsatisfactory points in view of activity and selectivity of a catalyst, namely, degree of conversion of cycloalkane and a selectivity coefficient of cycloalkanol and/or cycloalkanone. Thus, an object of the present invention is to provide a method capable of producing cycloalkanol and/or cycloalkanone with a favorable selectivity coefficient by oxidizing cycloalkane with favorable degree of conversion.

The present invention provides a method for producing cycloalkanol and/or cycloalkanone, which comprises oxidizing cycloalkane with oxygen in the presence of a catalyst, wherein the catalyst is a catalyst obtained by supporting metals of Groups 5 to 10 of the Periodic Table on a carrier, the carrier being subjected to a catalytic treatment with an organosilicon compound.

According to the present invention, cycloalkanol and/or cycloalkanone can be produced with a favorable selectivity coefficient by oxidizing cycloalkane with favorable degree of conversion.

DETAILED DESCRIPTION OF THE INVENTION

Figure 1:
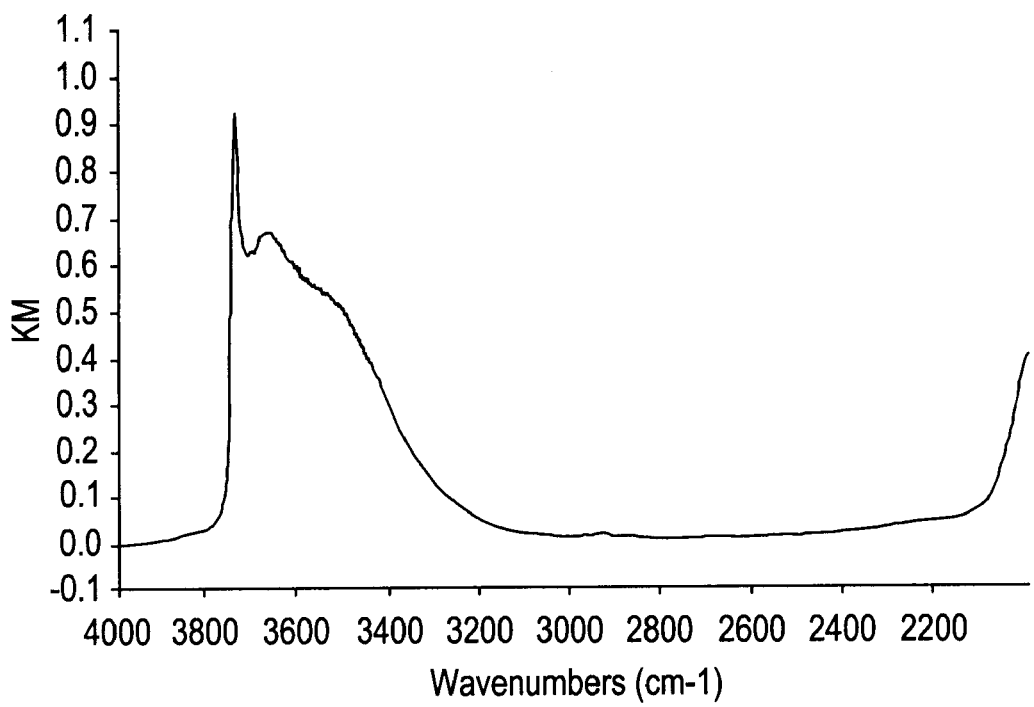
FIG. 1 is a graph showing an infrared absorption spectrum of a cobalt supported silica obtained in Reference Example 1.

The present invention will now be described in detail. In the present invention, corresponding cycloalkanol and/or cycloalkanone are produced by oxidizing cycloalkane used as a material with oxygen (molecular oxygen) in the presence of a catalyst.

Examples of the cycloalkane as the material include monocyclic cycloalkane having no substituent on the ring, such as cyclopropane, cyclobutane, cyclopentane, cyclohexane, cycloheptane, cyclooctane, cyclodecane, or cyclooctadecane; polycyclic cycloalkane such as decalin or adamantane, and cycloalkane having a substituent on the ring, such as methylcyclopentane or methylcyclohexane, and also two or more kinds of them can be used, if necessary.

An oxygen-containing gas is commonly used as an oxygen source. This oxygen-containing gas may be, for example, an air, pure oxygen, or an air or pure oxygen diluted with an inert gas such as nitrogen, argon or helium. Oxygen enriched air obtained by adding pure oxygen to an air can also be used.

In the present invention, the catalyst to be used is a catalyst obtained by supporting metals of Groups 5 to 10 of the Periodic Table on a carrier, the carrier being subjected to a catalytic treatment with an organosilicon compound. When such a catalyst is used, cycloalkanol and/or cycloalkanone can be produced with a favorable selectivity coefficient by oxidizing cycloalkane with favorable degree of conversion.

Examples of the metal to be supported on the carrier include vanadium, chromium, manganese, iron, cobalt, ruthenium and palladium. Among these metals, cobalt is preferably used. If necessary, one or more kinds of these metals may be used. The supporting rate of the metal is commonly from 0.01 to 20%, preferably from 0.05 to 10%, and still more preferably from 0.1 to 5%, in terms of a weight ratio of the metal to the carrier.

The carrier, on which the metal is supported, is preferably an oxide carrier and is preferably an oxide containing at least one element selected from magnesium, aluminum, silicon, titanium and zirconium. Among these oxides, silicon dioxide, namely, silica is preferably used.

Examples of the method of supporting the metal on the carrier include a method of impregnating a carrier with a solution of a metal compound such as halide, carboxylate or oxo acid salt of the metal, a method of immersing a carrier in a solution of a metal compound such as halide, carboxylate or oxo acid salt of the metal thereby adsorbing the metal compound to the carrier, and a method of ion-exchanging a metal cation of a metal compound with a cation of a carrier.

The organosilicon compound used in a catalytic treatment of the carrier can preferably react with the carrier thereby bonding on the surface of the carrier, and can be typically represented by the following formula (1):

$$Si(R^1)_x(R^2)_{4-x} \qquad (1)$$

wherein $R^1$ represents an alkoxy group, a hydroxy group or a halogen atom, $R^2$ represents an alkoxy group, an alkyl group, an allyl group, an aryl group or an aralkyl group, and x represents a number of 1 to 3.

Examples of the alkoxy group represented by $R^1$ and $R^2$ include methoxy group, ethoxy group, propoxy group and butoxy group, and examples of the alkyl group represented by $R^2$ include methyl group, ethyl group, propyl group and butyl group. Examples of the aryl group represented by $R^2$ include phenyl group, naphthyl group and tolyl group, and examples of the aralkyl group represented by $R^2$ include benzyl group and phenetyl group.

As the organosilicon compound represented by the formula (1), for example, a compound wherein all $R^1$ and $R^2$ are alkoxyl groups, namely, an alkyl ester of orthosilicic acid is preferably used.

The method of subjecting a carrier to a catalytic treatment with an organosilicon compound includes, for example, a method of immersing a carrier in a liquid containing an organosilicon compound and a method of bringing a gas containing an organosilicon compound into contact with a carrier.

The amount of the organosilicon compound used is commonly from 1 to 10,000 parts by weight, preferably from 5 to 1,000 parts by weight, and still more preferably from 10 to 500 parts by weight, based on 100 parts by weight of the carrier.

The temperature of the catalytic treatment is commonly from 0 to 300° C., and preferably from 30 to 250° C. The time of the catalytic treatment is commonly from 0.1 to 50 hours, and preferably from 1 to 20 hours.

The catalytic treatment of the carrier with the organosilicon compound may be conducted before or after supporting the metal, or can be conducted simultaneously with supporting of the metal. Commonly, the catalytic treatment is preferably conducted after supporting the metal.

The oxidation reaction of cycloalkane can be conducted by bringing cycloalkane into contact with oxygen in the presence of the metal supported catalyst thus obtained. The amount of the catalyst used is commonly from 0.01 to 50 parts by weight, and preferably from 0.1 to 10 parts by weight, based on 100 parts by weight of cycloalkane.

The reaction temperature is commonly from 0 to 200° C., and preferably from 50 to 170° C., and the reaction pressure is commonly from 0.01 to 10 MPa, and preferably from 0.1 to 2 MPa. The reaction solvent can be optionally used and, for example, a nitrile solvent such as acetonitrile or benzonitrile, and a carboxylic acid solvent such as acetic acid or propionic acid can be used.

The after-treatment after the oxidation reaction is not specifically limited and includes, for example, a method of filtering the reaction mixture thereby separating a catalyst, followed by washing with water and further distillation. In case the reaction mixture contains cycloalkyl hydroperoxide corresponding to cycloalkane, cycloalkyl hydroperoxide can be converted into the objective cycloalkanol and cycloalkanone by an alkali treatment or a reduction treatment.

EXAMPLES

Examples of the present invention will now be described, but the present invention is not limited thereto. Cyclohexane, cyclohexanone, cyclohexanol and cyclohexyl hydroperoxide in the reaction solution were analyzed by gas chromatography, and the degree of conversion of cyclohexane as well as each selectivity coefficient of cyclohexanone, cyclohexanol and cyclohexyl hydroperoxide were calculated from the analysis results.

Reference Example 1

2.51 g of fumed silica (manufactured by ALDRICH Co.), 4.18 g of cobalt (II) acetate tetrahydrate (manufactured by Wako Pure Chemical Industries, Ltd.) and 37.27 g of water were charged in a 300 ml flask and then stirred at 47° C. for 3 hours. The resulting mixture was cooled to room temperature and then filtered. The residue washed with water and dried at 100° C. to obtain a cobalt supported silica. An infrared absorption spectrum of the resulting cobalt supported silica was measured by the following procedure. The results are shown in FIG. 1.

[Measurement of Infrared Absorption Spectrum]

A cobalt supported silica was charged in a catalytic cell (Diffuse Reflectance Heat Chamber, Model HC900, manufactured by SPECTRA-TECH Co.) and set in an apparatus for measuring an infrared absorption spectrum (Magna 760-ESP, manufactured by NICOLET Co.) and, after deaeration at 200° C. for one hour, an infrared absorption spectrum was measured. The measuring conditions are as follows: the measuring temperature is 200° C., the measuring pressure is 0.1 Torr (13 Pa), the measuring range is from 400 to 4,000 cm$^{-1}$, and the resolving power is 4 cm$^{-1}$. Using data obtained by measuring an infrared absorption spectrum of potassium bromide in the same manner as a background, the resulting data were subjected to Kubelka-Munk conversion.

Reference Example 2

Figure 2:
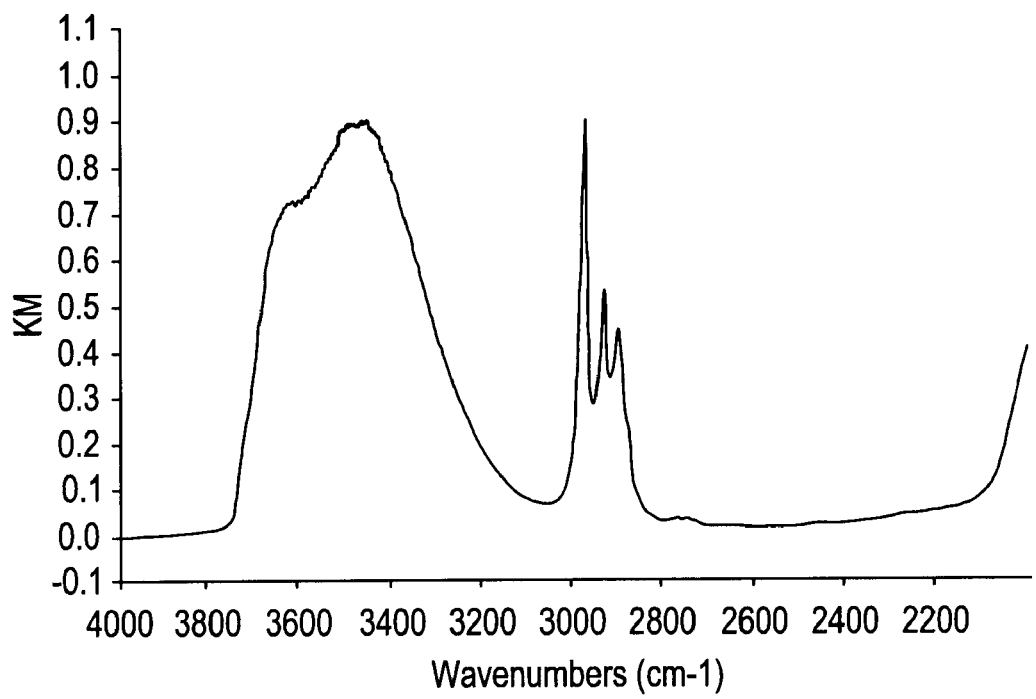
FIG. 2 is a graph showing an infrared absorption spectrum of a cobalt supported silica subjected to a catalytic treatment with ethyl orthosilicate obtained in Reference Example 2.

0.2 g of the cobalt supported silica obtained in Reference Example 1 and 2.0 g of ethyl orthosilicate (manufactured by Wako Pure Chemical Industries, Ltd.) were charged in a flask and then stirred under a nitrogen atmosphere at 90° C. for 7 hours and a half. The resulting mixture was cooled to room temperature and ethanol was added, followed by stirring and further filtration. The residue washed with acetone, dried under 0.1 Torr (13 Pa) at 40° C. for 2 hours and then dried at 60° C. An infrared absorption spectrum of the resulting cobalt supported silica subjected to a catalytic treatment with ethyl orthosilicate was measured in the same manner as in Reference Example 1. The results are shown in FIG. 2.

As shown in FIG. 1, a peak attributed to a so-called terminal silanol group is observed at about 3740 cm$^{-1}$ in the cobalt supported silica obtained in Reference Example 1, while the same peak is not observed in the cobalt supported silica subjected to a catalytic treatment with ethyl orthosilicate obtained in Reference Example 2 and it is considered that the terminal silanol group is silylated with ethyl orthosilicate.

Example 1

In a 300 ml autoclave, 100 g (1.2 mol) of cyclohexane and 0.1 g of the cobalt supported silica subjected to a catalytic treatment with ethyl orthosilicate obtained in Reference Example 2 were charged. After increasing the pressure in the system to 0.93 MPa at room temperature using nitrogen and heating to 130° C., the reaction was carried out under the flow of a gas having an oxygen concentration of 5 vol % for 8 hours.

5 hours after the beginning of the reaction, the degree of conversion of cyclohexane was 5.4%, the selectivity coefficient of cyclohexanone was 26.6%, the selectivity coefficient of cyclohexanol was 46.6%, and the selectivity coefficient of cyclohexyl hydroperoxide was 13.7% (total electivity coefficient: 8 6.9%). 8 hours after the beginning of the reaction (upon completion), the degree of conversion of cyclohexane was 9.3%, the selectivity coefficient of cyclohexanone was 35.1%, the selectivity coefficient of cyclohexanol was 43.0%, and the selectivity coefficient of cyclohexyl hydroperoxide was 5.9% (total selectivity coefficient: 84.0%).

Comparative Example 1

The same operation as in Example 1 was conducted, except that the cobalt supported silica obtained in Reference Example 1 was used in place of the cobalt supported silica subjected to a catalytic treatment with ethyl orthosilicate obtained in Reference Example 2.

5 hours after the beginning of the reaction, the degree of conversion of cyclohexane was 5.9%, the selectivity coefficient of cyclohexanone was 30.2%, the selectivity coefficient of cyclohexanol was 48.7%, and the selectivity coefficient of cyclohexyl hydroperoxide was 3.4% (total selectivity coefficient: 82.3%). 8 hours after the beginning of the reaction (upon completion), the degree of conversion of cyclohexane was 9.4%, the selectivity coefficient of cyclohexanone was 36.6%, the selectivity coefficient of cyclohexanol was 42.9%, and the selectivity coefficient of cyclohexyl hydroperoxide was 1.9% (total selectivity coefficient: 81.4%).

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description but is only limited by the scope of the appended claims.

What is claimed is

1. A method for producing cycloalkanol and/or cycloalkanone, which comprises oxidizing cycloalkane with oxygen in the presence of a catalyst at a temperature of from 50 to 200° C., wherein the catalyst is a catalyst obtained by supporting metals of Groups 5 to 10 of the Periodic Table on a carrier, the carrier being immersed in a liquid containing an organosilicon compound or being contacted with a gas containing an organosilicon compound, and the organosilicon compound is represented by the following formula (1):

$$Si(R^1)_x(R^2)_{4-x} \qquad (1)$$

wherein $R^1$ represents an alkoxy group, a hydroxy group or a halogen atom, $R^2$ represents an alkoxy group, an alkyl group, an allyl group, an aryl group or an aralkyl group, and x represents a number of 1 to 3.

2. The method according to claim 1, wherein the metal is selected from vanadium, chromium, manganese, iron, cobalt, ruthenium and palladium.

3. The method according to claim 1, wherein the metal is cobalt.

4. The method according to any one of claims 1 to 3, wherein the carrier is an oxide containing an element selected from magnesium, aluminum, silicon, titanium and zirconium.

5. The method according to any one of claims 1 to 3, wherein the carrier is silica.

6. The method according to any one of claims 1 to 3, wherein the organosilicon compound is alkyl orthosilicate.

7. The method according to any one of claims 1 to 3, wherein the cycloalkane is cyclohexane.

8. The method according to claim 1, wherein the cycloalkane oxidizing temperature is from 50 to 170° C.

* * * * *

UNITED STATES PATENT AND TRADEMARK OFFICE
CERTIFICATE OF CORRECTION

| | | |
|---|---|---|
| PATENT NO. | : 7,541,500 B2 | Page 1 of 1 |
| APPLICATION NO. | : 11/710413 | |
| DATED | : June 2, 2009 | |
| INVENTOR(S) | : Masahiro Hoshino | |

It is certified that error appears in the above-identified patent and that said Letters Patent is hereby corrected as shown below:

On the title page item "(56)", under FOREIGN PATENT DOCUMENTS, please insert the following foreign reference:

--EP    0 916 403 A2    5/19/1999--

Signed and Sealed this

Sixth Day of October, 2009

David J. Kappos
*Director of the United States Patent and Trademark Office*